United States Patent [19]
Graybill et al.

[11] Patent Number: 5,146,014
[45] Date of Patent: Sep. 8, 1992

[54] PERFLUOROETHYLDIMETHYL CYCLOHEXANE

[75] Inventors: John K. Graybill, Macungie; Gregory B. George, New Ringgold, both of Pa.

[73] Assignee: Air Products and Chemicals, Inc., Allentown, Pa.

[21] Appl. No.: 724,613

[22] Filed: Jul. 2, 1991

[51] Int. Cl.$^5$ .................... C07C 22/00; C07C 23/10; C07C 17/02; C07C 17/10
[52] U.S. Cl. ............................ 570/131; 228/42; 228/218
[58] Field of Search ........................ 570/131

[56] References Cited

U.S. PATENT DOCUMENTS

| | | | |
|---|---|---|---|
| 2,606,212 | 8/1952 | McBee et al. | 260/648 |
| 4,453,028 | 6/1984 | Lagow | 570/131 |
| 4,801,761 | 1/1989 | Bailey et al. | 570/130 |

FOREIGN PATENT DOCUMENTS 2110204  6/1983  United Kingdom ............... 570/131

*Primary Examiner*—Joseph E. Evans
*Attorney, Agent, or Firm*—Geoffrey L. Chase; James C. Simmons; William F. Marsh

[57] ABSTRACT

A novel composition of matter is disclosed comprising perfluorinated, ethyldimethyl cyclohexane. The compound has unique utilities in vapor phase heating and soldering, oxygen transport for biological fluids and other requirements for an inert, stable fluid.

6 Claims, No Drawings

PERFLUOROETHYLDIMETHYL CYCLOHEXANE

FIELD OF THE INVENTION

The present invention is directed to a novel composition comprising perfluoroethyldimethyl cyclohexane. More specifically, the present invention is directed to perfluoro-1-ethyl-2,4-dimethyl cyclohexane. The composition has utility for vapor phase soldering, gas transport, lubrication additive and applications where an inert fluid is necessary.

BACKGROUND OF THE PRIOR ART

Various prior art compounds have been synthesized and more specifically fluorinated to provide at least partially fluorinated organic compounds having a high degree of heat stability. For instance, in U.S. Pat. No. 2,606,212, compounds are disclosed which are derivatives of cyclohexane having full substitution of any hydrogen with fluorine and with various alkyl radicals on the cyclohexane ring. For example, perfluoro-1,2,4-trimethyl cyclohexane is disclosed in the patent, and perfluoro-1,3-diethyl-5-methyl cyclohexane is disclosed in the patent. However, compounds such as these have not satisfied particular needs for an inert fluid having a precise boiling point, vapor pressure and gas transport capabilities as is provided by the present invention which is set forth below.

BRIEF SUMMARY OF THE INVENTION

The present invention is a perfluorinated compound having the following structure wherein the ring carbons are fully fluorinated:

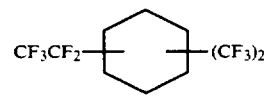

Preferably, the present invention is a compound having the following structure:

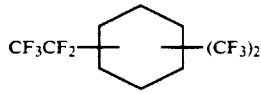

Preferably, the present invention is a compound having the following structure:

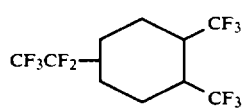

Alternatively, the present invention is a compound having the following structure:

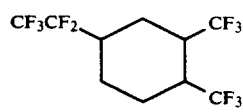

Alternatively, the present invention is a compound having the following structure:

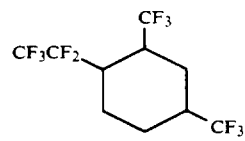

Further alternatively, the present invention is a compound having the following structure:

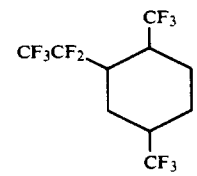

The present invention is also a method of soldering wherein a component to be soldered is immersed in a vapor bath to melt the solder, and the component is then withdrawn from the vapor bath, the improvement comprising that the vapor bath is composed substantially of perfluorinated compounds of the formula:

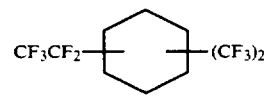

The present invention is also a method of transporting gases in a fluid system, the improvement comprising using as the gas transport agent a perfluorinated compound of the formula:

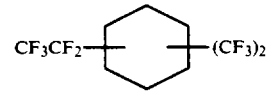

DETAILED DESCRIPTION OF THE INVENTION

The new composition of matter of the present invention comprising ethyl dimethyl cyclohexane in a perfluorinated or fully fluorinated condition is of interest because the boiling point is comparable to perfluorodecalin, but has physical properties that differ such as pore point and surface tension. These significantly differing properties from perfluorodecalin provide enhanced utility for such applications as improved transport of biological samples through conduits or tubing because of the low surface tension of the compound of the present invention of 17.4 dynes/cm at 25° C. versus 19.3 dynes/cm at 25° C. for perfluorodecalin. The NMR[19]F spectrum is 3.0 for $CF_3$, 3.1 for $CF_2$, and 1.0 CF.

The various perfluorinated ethyldimethyl derivatives of cyclohexane, which constitute the subject matter of the present invention, are valuable as inert constant boiling fluids required by the electronic fabrication industry for the manufacture and testing of various electronic components. Fluids boiling in the temperature range of 140°-145° C., are of interest to the electronics industry for these applications. Currently, various suppliers of fluorinated fluids provide a series of compounds that meet the 150°-265° C., temperature range which are based on, for example, perfluorinated tertiary amines. There is some question on the stability of these materials at elevated temperatures. One concern arises from incomplete fluorination, which results in residual hydrogen. These partially fluorinated compounds have been shown to undergo decomposition at elevated temperatures resulting in the formation of HF and perfluoroisobutylene.

Another class of compounds that are currently supplied to meet the needs for boiling fluids are based on perfluoropolyethers. These polyethers are prepared by the oxidative polymerization of tetrafluoroethylene. To obtain the various boiling ranges, the polyethers are distilled into different fractions. The final product does not constitute a single compound, but rather a mixture of molecular weight ranges. This results in a product, that with time will increase in boiling temperature at the lower molecular weight fractions are removed by differential boil-off.

The compositions of the present invention constitute essentially single compounds having sharply defined boiling points which do not fractionate off into various components through exposure to cycling from cooldown to high temperature utilization, such utilization as is characteristic of vapor phase soldering fluid unity.

The perfluoroethyldimethyl cyclohexane compound of the present invention which is preferably substituted with methyl at the number 2 and 4 position of the cyclohexane ring has an empirical formula of $C_{10}F_{20}$ and a molecular weight of 500. The material is a liquid at room temperature with a boiling point of approximately 146° C. The general structure of the compound of the present invention has been confirmed by $^{19}F$ NMR (nuclear magnetic resonance spectroscopy) and GC/MS (gas chromatography/mass spectroscopy). Typically, the feedstock to produce such a perfluorinated compound is the hydrocarbon ethyldimethyl cyclohexane, which can be prepared by the alkylation of cyclohexane by known techniques. The present compounds have also been found to be cleavage products of the fluorination process for producing perfluoro-1, 1-di(orthoxylyl) ethane in accordance with U.S. Pat. No. 4,801,761 which is incorporated by reference herein. The new composition of the present invention is substantially a perfluorinated analog of the ethyldimethyl cyclohexane hydrocarbon starting material wherein all aromatic character and hydrogen are removed as a result of the reaction process. All isomers and conformers of ethyldimethyl cyclohexane are represented by the perfluorinated compound of the present invention.

All of these species of the compounds of the present invention have utility for oxygen transport media for in vivo and in vitro use as pure substances or mixtures or emulsions, as well as use as hydraulic fluids, lubricants, heat exchange or cooling fluids and other such applications where chemical inertness and boiling point are the desired physical and chemical properties, most particularly vapor phase soldering. Various of the compounds have been tested as vapor phase soldering fluids. The fluids were heated at reflux for an extended period of time and showed no evidence of decomposition, wherein a printed circuit board which contained a soldering silk screen and a surface mounted device was immersed into the reflux vapor area and the solder reflow occurred within 30 seconds. This demonstrated successful and acceptable vapor phase soldering utility.

At this time, the preparation and identification of the compounds of the present invention will be set forth in the following examples and tables.

EXAMPLE 1

In a typical reaction 1,1-di(orthoxylyl) ethane is vaporized to a cobalt trifluoride reactor operating at 230° to 350° C. The resulting fluorochemical product, containing perfluoro-1,1-di(orthoxylyl) methane is collected and separated from hydrogen fluoride by-products. The fluorochemical is distilled to give a spectrum of products. The fluorination process predominantly cleaves the methyl group from the bridging chain between the two ring constituents to change the ethyl bridge to a methylene bridge, but a mixture of the ethyl and methylene bridge compounds are produced which are separated by distillation. Milder fluorination conditions increases the amount of ethyl bridged compound. Cleavage at the bond between the bridge and the ring gives the present compound. Perfluoroethyldimethyl cyclohexane is found as a distillation cut of the fluorination product.

EXAMPLE 2

77 g of 1,1-di(orthoxylyl) ethane was heated to its boiling point in a vaporizer while purging with nitrogen gas. The 1,1-di(orthoxylyl) ethane/nitrogen gas stream was fed to a heated reactor 6" in diameter and 4' long containing approximately 35 lbs. of cobalt trifluoride. The reactor was held at approximately 345° C., in the first half of the reactor and approximately 415° C., in the last half of the reactor. The 1,1-di(orthoxylyl) ethane feed was subsequently converted to 162 g of a perfluorochemical. The crude fluorochemical was filtered to remove any solids and pass thru alumina to remove any active fluorides. A portion of the product distilling at 140°-145° C. is the compound of the present invention.

EXAMPLE 3

143 g of 1,1-di(orthoxylyl) ethane was heated to its boiling point in a vaporizer while purging with nitrogen gas. The 1,1-di(orthoxylyl) ethane/nitrogen gas stream was fed to a heated reactor 6" in diameter and 4' long containing approximately 35 lbs. of cobalt trifluoride. The reactor was held at approximately 345° C., in the first half of the reactor and approximately 415° C., in the last half of the reactor. The 1,1-di(orthoxylyl) ethane feed was subsequently converted to 201 g of a perfluorochemical. The crude fluorochemical was filtered to remove any solids and passed thru alumina to remove any active fluorides.

EXAMPLE 4

215 g of a crude perfluorochemical prepared in a similar manner to Examples 2 and 3 above was distilled through a glass packed column. A product was collected which had a boiling range of 140°-145° C. Analysis by $^{19}F$ NMR spectroscopy and GC/MS (gas chromatography/mass spectroscopy) confirmed the presence of perfluoroethyldimethyl cyclohexane.

The compounds can also be synthesized by other fluorination techniques, including direct fluorination with elemental fluorine under mild conditions, as well as fluorination using other fluorine sources than cobalt trifluoride. As stated previously, the compounds display unique stability and appropriate high temperature boiling point to make them useful for vapor phase soldering, particularly of solder fluxes that melt slightly below the boiling point of the compounds.

In a vapor phase soldering, a component is typically affixed to a pretreated substrate. Such component or article can constitute a miniaturized electronic component such as an integrated circuit or transistor, or the like, wherein the article is assembled to a substrate, such as printed circuit board or hybrid circuit board, with a solder preform or is adhered to such substrate with a solder paste while the paste is still in a tacky state. After the preform and article are assembled, or the article is adhered and the paste is dry, the assembly is then placed in the vapor zone of a container of the boiling vapor phase soldering working fluid; perfluoro ethyl dimethyl cyclohexane. The vapor of the compound as it boils is heavier than air and therefore will tend to remain in a settled condition over the bath of boiling liquid. The vapor will maintain the temperature of the boiling point of the liquid and upon immersion of the article, component or assembly into the vapor zone, the vapor will condense on the relatively cooler article, assembly or component and thereby impart the heat of vaporization of the condensing vapor on the article, assembly or component. The heat of the vapor, being limited to the boiling point of the liquid compound, will control the maximum heat that the article, assembly component is subjected to, and this heat is designed to be approximately 30° C., above the melting point of the solder preform or solder paste. The effect is that the solder is melted and appropriately solders the joint of the article, assembly or component, while avoiding any detrimental high heat effects to the other portions of the article, assembly or component. The soldered article, assembly or component is then removed from the fluid vapor and cooled under preferably ambient conditions, or alternately, a second fluid medium which is below the melting point of the solder is utilized to preform such cooling function.

Alternatively, the same working fluid comprising perfluoro ethyl dimethyl cyclohexane thereof can be utilized in wave soldering wherein the article or component does not utilize a solder preform or solder paste, but rather is assembled by pins into a substrate such as a circuit board wherein the article or component is immersed in the vapor of the working fluid sufficient to heat the article to near solder reflow conditions. Then the portions of the assembly, article or component so as to solder contacts or pins of the article or component to, potentially, a substrate such as a circuit pattern of printed circuit board.

Integrated soldering of surface mounted components and through-hole components in a simultaneous reflow and solder spray technique, can also be performed in the vapor of perfluoro ethyl dimethyl cyclohexane. In such a technique, some components on a board art soldered by the heat of the condensing vapor compound, thereby reflowing solder preforms or solder paste, while other through-hole components are soldered by the application of molten solder to the underside of the circuit board. The solder application can be from a wave or a spray of solder. The solder in the application technique can be heated by a source other than the perfluoro ethyl dimethyl cyclohexane.

The technique for soldering, fusing or brazing with a working fluid constituting perfluoro ethyl dimethyl cyclohexane wherein the vapor phase of the working fluid condenses on the article or component in order to transfer the heat of vaporization to the article or component for the purposes of soldering, fusing or brazing provides an attractive and advantageous method for performing these operations, such as was not available to the prior art. The preferred mode of operation constitutes the condensation soldering or wave soldering of components using such a compound as the heat transfer media and these techniques may be utilized in either a batch or continuous mode. The compound provides an unexpectedly good match of the characteristics which are known to be required of a working fluid for operation in this field. Specifically, the compound has a boiling point at least equal to or preferably above the melting point of tin-silver solders presently widely utilized in the electronic component industry for assembly of certain electronic components. When in the pure form of the desired perfluoro ethyl dimethyl cyclohexane, the working fluid should have a well defined boiling point, which provides better temperature control over the process. It is preferred to operate the process with highly pure perfluoro ethyl dimethyl cyclohexane so as to effectively have a single component working fluid. However, it is understood that nondetrimental amounts of isomers and impurities may be incorporated into the compound working fluid without departing from the invention. Vapor phase soldering is described in U.S. Pat. No. Re. 30,399 and U.S. Pat. No. 4,549,686, both of which are incorporated herein by reference.

The compounds of the present invention succeed in overcoming the drawbacks of various of the compounds of the prior art, particularly for utility in vapor phase soldering fluid use. The compounds of the present invention exhibit all of the desired attributes of a vapor phase soldering fluid as identified in U.S. Pat. No. Re. 30,399 described above. Included in these attributes which the compounds in the present invention exhibit are: low toxicity, chemical inertness, lack of flammability, appropriate dielectric characteristics, degreasing properties, sharply defined boiling point, a vapor denser than air and relatively high latent heat of vaporization. Specifically, these compounds have low potential for evolution of HF and perfluoroisobutylene when subjected to long term cyclic heating and cooling typical of vapor phase soldering use.

The compounds of the present invention also have utility as an inert carrier fluids for the testing of biological samples such as blood samples, in automated analysis instruments where individual biological samples are conveyed and/or separated by the perfluoroethyl-dimethyl cyclohexane as an inert carrier fluid which keeps the samples as discrete portions as the analysis is performed on multiple samples in a continuous process. Additionally, the compounds can be used as transport agents for oxygen in artificial blood, culture media or perfusates for donor organs, where they substitute for existing agents, such as perfluorodecalin and perfluorooctylbromide.

The compounds of the present invention include perfluoro-1-ethyl-2, 4-dimethyl cyclohexane, perfluoro-1-ethyl-2, 5-dimethyl cyclohexane and perfluoro-1-ethyl-3, 4-dimethyl cyclohexane as the preferred isomers.

The present invention has been set forth with regard to various specific examples and embodiments of the invention. However, the scope of the invention should be ascertained from the claims which follow.

We claim:

1. The perfluorinated compound having the following structure wherein the ring carbons are fully fluorinated.

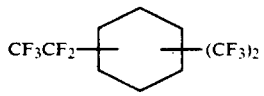

2. The invention of claim 1 wherein the compound has the following structure:

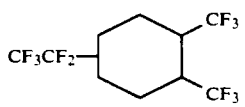

3. The invention of claim 1 wherein the compound has the following structure:

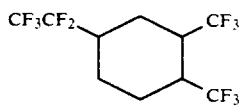

4. The invention of claim 1 wherein the compound has the following structure:

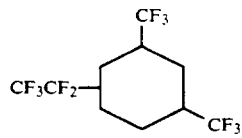

5. The invention of claim 1 wherein the compound has the following structure:

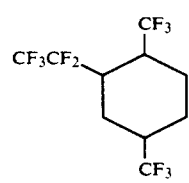

6. The invention of claim 1 wherein the compound has the following structure:

* * * * *